United States Patent [19]
Richardson

[11] Patent Number: 5,339,533
[45] Date of Patent: Aug. 23, 1994

[54] SYSTEM FOR MEASURING STIFFNESS OF A FRACTURED BONE

[76] Inventor: James B. Richardson, 55 Glenfrith Close, Leicester LF3 900, United Kingdom

[21] Appl. No.: 163,426

[22] Filed: Dec. 8, 1993

Related U.S. Application Data

[63] Continuation of Ser. No. 86,147, Jul. 1, 1993, abandoned.

[51] Int. Cl.$^5$ ............................................. A61B 5/103
[52] U.S. Cl. ..................................... 33/512; 128/782
[58] Field of Search .................. 128/774, 782; 33/511, 33/645, 512, 515, 806

[56] References Cited

U.S. PATENT DOCUMENTS

| | | | |
|---|---|---|---|
| 2,333,033 | 10/1943 | Mraz | 33/645 |
| 3,229,372 | 1/1966 | Quashnock et al. | 33/512 |
| 4,033,043 | 7/1977 | Cunningham | 33/806 |
| 5,082,003 | 1/1992 | Lamb et al. | 33/512 |
| 5,121,753 | 6/1992 | Pacz | 33/515 |
| 5,163,228 | 11/1992 | Edwards | 33/512 |
| 5,171,248 | 12/1992 | Ellis | 33/512 |

FOREIGN PATENT DOCUMENTS

| | | |
|---|---|---|
| 0324279 | 7/1989 | European Pat. Off. . |
| WO8601588 | 3/1986 | World Int. Prop. O. . |

OTHER PUBLICATIONS

Biometrics, "Instrumentation for the data acquisition and analysis of human activity."
Biometrics, "Computer Games Get Physical!!!".
Kenwright, et al., "Axial Movement and Tibial Fractures," The Journal of Bone and Joint Surgery, vol. 73-B, No. 4, 1991, pp. 654-659.
Cunnigham et al., "The Measurement of Stiffness of Fractures treated With External Fixation," Engineering Medicine, vol. 16, No. 4, 1987, pp. 229-232.
Bourgois, "Unusual Sensors in Unusual Mechanical Applications," Journal A, vol. 24, No. 3, 1983, pp. 139-153.
James et al., "A Clinical Electrogoniometry System," Engineering In Medicine, vol. 11, No. 3, 1982, pp. 123-124.

Primary Examiner—William Cuchlinski, Jr.
Assistant Examiner—G. Bradley Bennett
Attorney, Agent, or Firm—Hopgood, Calimafde, Kalil & Judlowe

[57] ABSTRACT

A bone-stiffness measuring instrument comprises a set or kit of readily assembled and adjusted components, namely a goniometer, a light-weight load cell, and a small computer package, adapted to continuously respond to the outputs of the load cell and goniometer and to display and/or record (i.e., store) measured stiffness data; plus hardware in duplicate, namely, a bone-screw clamp and bracket for fixed reference to bone-screws that are externally exposed on each of the respective sides of the fracture (following removal of an external fixator), a stiff arcuate arm member of radius at least twice the diameter of the fractured bone, and a goniometer-end mount. The arcuate arm member is adjustably fixed to the bracket for bone-screw reference, and the goniometer-end mount is also adjustably fixed to the arcuate arm member, with a releasably lockable ball-joint connection for adjusted orientation of an end mounting to the goniometer.

45 Claims, 3 Drawing Sheets

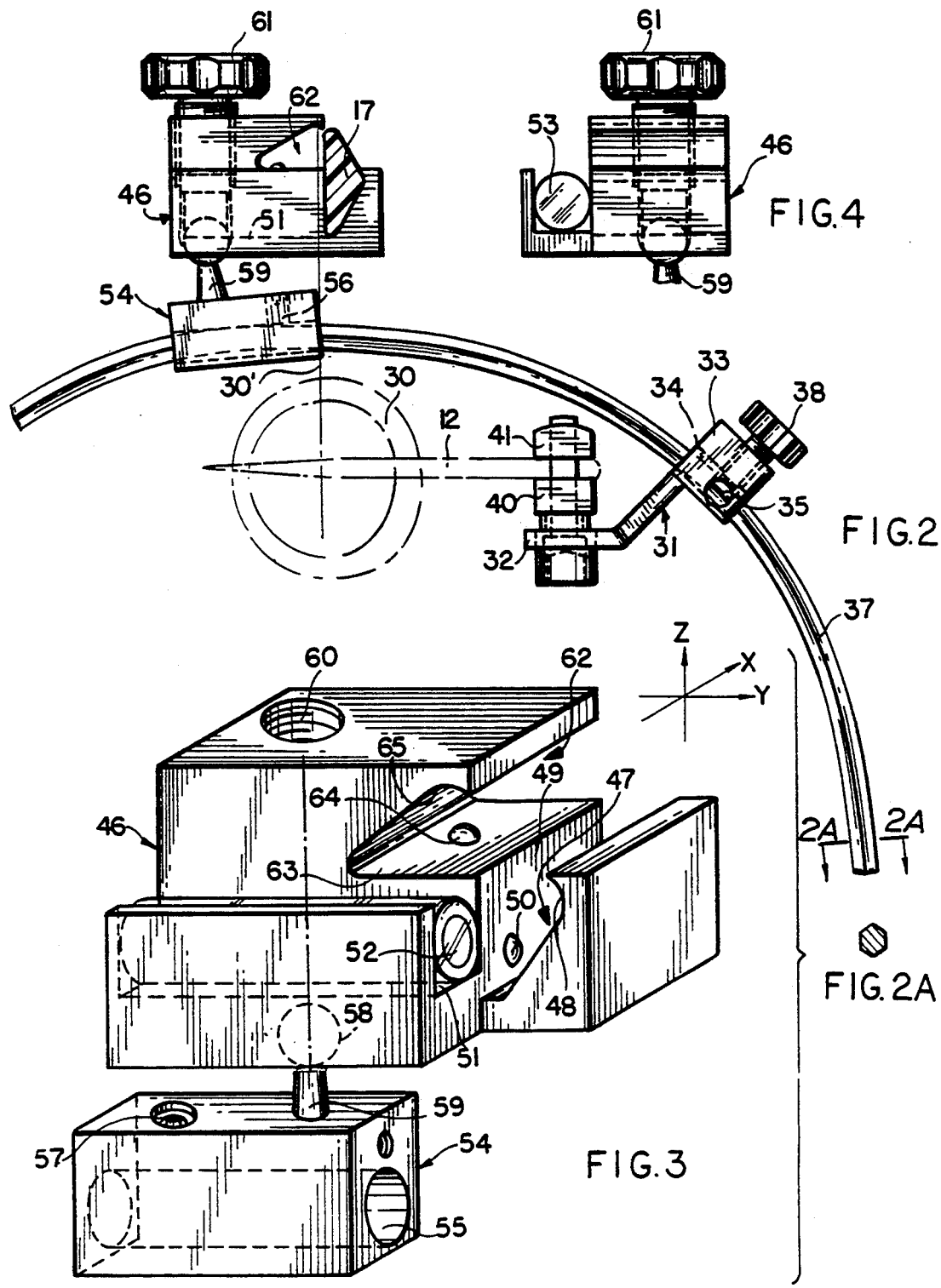

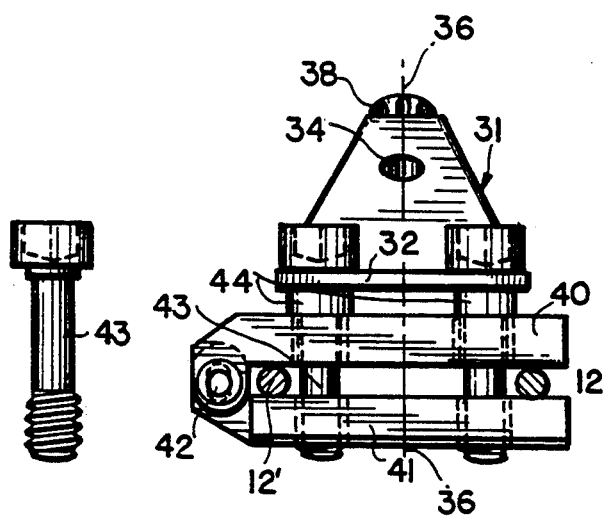
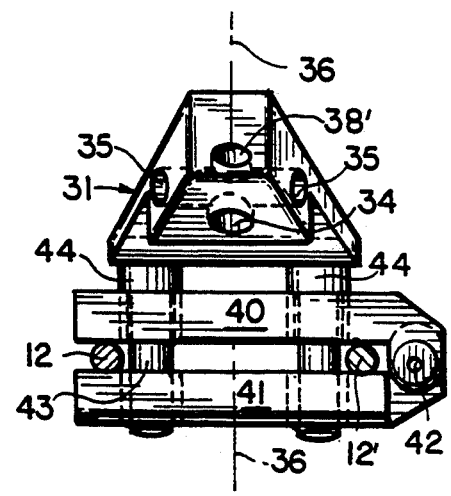
FIG.5A  FIG.5  FIG.6
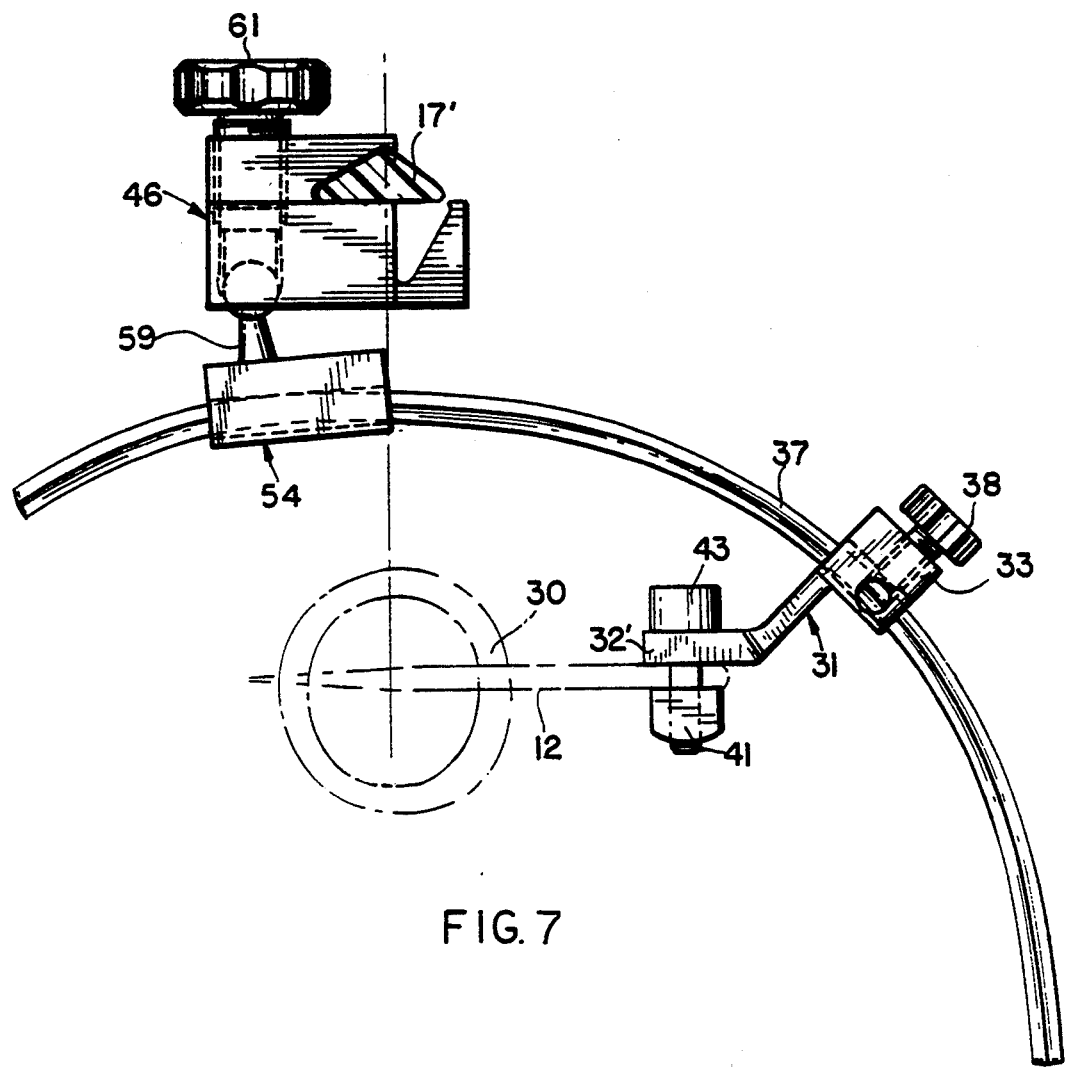
FIG.7

SYSTEM FOR MEASURING STIFFNESS OF A FRACTURED BONE

This application is a continuation of application Ser. No. 08/086,147, now abandoned, filed Jul. 1, 1993.

BACKGROUND OF THE INVENTION

The invention relates to apparatus for measuring stiffness of a fractured bone in the course of bone healing, wherein the healing has been aided by an external fixator for retention of the broken segments.

To date most of the clinical data and research on bonefracture healing with external fixation have been concerned with measurements on the tibia, because of the frequency of tibia fracture and the need to restore weight-bearing capability at the repaired site. Thus, in the present discussion, the tibia will be considered illustratively, since principles applicable to the tibia are applicable to other bones in the course of fracture repair.

The paper entitled: "The Measurement of Stiffness of Fractures Treated With External Fixation", Cunningham, et al., *Engineering in Medicine*, Vol. 16, No. 4, 1987, describes apparatus and a technique for indirectly measuring fracture stiffness, periodically in the course of healing a fractured tibia, wherein the patient is seated and rests the heel of his broken limb on a load cell so that the fractured bone, including its external fixator, are otherwise unsupported. The fixator is equipped with a transducer which is able to measure bending as a function of vertically downward force application to the leg. This technique has the disadvantage that even if bone-screw anchorages retain their fidelity, the deflection measurement must include a correctional calculation which reflects the fact that primary stiffness is in the fixator. Bone-stiffness measurement is thus indirect, and as a practical matter, the need to stress the bone in order to stress the fixator is the occasion for progressive deterioration of the effectiveness of bone-screw anchorage, resulting in progressive loss of measurement accuracy. To forestall the loss of bone-screw anchorage, one must severely limit the number and frequency of such measurements.

Published European Patent Application A0,324,279 describes apparatus for direct measurement of bone stiffness in circumstances generally similar to those of the Cunningham, et al, article, except that for purposes of making the deflection measurement, the fixator used for aiding fracture repair is temporarily removed, leaving fixator bone screws in place; and brackets releasably clamped to the bone screws provide proximal and distal points of support for the respective end mounts of a flexible elongate goniometer. The goniometer is the only external connection between the bone stubs on longitudinally opposite sides of the fracture, and therefore deflections measured for the vertically downward force applied to the limb at the fracture site are direct measurements, requiring no compensating calculation for fixator or goniometer stiffness, because the goniometer structure is inherently flexible and limp, and of negligible stiffness.

Despite the potential for direct measurement afforded by the structure of said published European patent application, the apparatus is structurally relatively crude, and therefore repeatability of measurements at any given occasion is somewhat open to chance, particularly in respect of desired alignment and orientation of the mounting ends of the goniometer, with respect to each other and with respect to the fractured bone.

BRIEF STATEMENT OF THE INVENTION

It is an object of the invention to provide improved apparatus for making bone-stiffness measurements of the character indicated.

A specific object is to provide apparatus meeting the above object and featuring repeatable accuracy and consistency of stiffness measurements to a degree that has previously been unavailable.

Another specific object is to meet the above objects with apparatus lending itself to ready assembly and disassembly, without requiring specialized tooling, and sufficiently portable when disassembled to allow the orthopedic specialist to carry, in a light-weight case, all components needed to assemble, use and disassemble the apparatus at each of a relatively large plurality of patient locations in a single day of varied bone-stiffness measurement visits.

The invention achieves these objects by providing a set or kit of readily assembled and adjusted components, namely: a goniometer, a light-weight load cell, and a small computer package, adapted to continuously respond to the outputs of the load cell and goniometer and to display and/or record (i.e., store) measured stiffness data; plus hardware in duplicate, namely, a bone-screw clamp and bracket for fixed reference to bone-screws that are externally exposed on each of the respective sides of the fracture (following removal of an external fixator), a stiff arcuate arm member of radius at least twice the diameter of the fractured bone, and a goniometer-end mount. The arcuate arm member is adjustably fixed to the bracket for bone-screw reference, and the goniometer-end mount is also adjustably fixed to the arcuate arm member, with a releasably lockable ball-joint connection for adjusted orientation of an end mounting to the goniometer.

DETAILED DESCRIPTION

A preferred embodiment of the invention will be described in detail, in conjunction with the accompanying drawings, in which:

FIG. 2 is an enlarged simplified view in axially viewed elevation, namely, in a plane 2—2 normal to the local axis of the fractured bone of FIG. 1, showing the relation of connected parts that provide support for one of the mounted ends of a goniometer;

FIG. 2A is a section of a part of FIG. 2, taken at 2A—2A;

FIG. 3 is a further enlarged isometric diagram of a goniometer-end mount in FIG. 2;

FIG. 4 is a view in right-side elevation of the goniometer-end mount of FIG. 2, to the scale of FIG. 2;

FIG. 5 is a view in side elevation of a bone-screw clamp and arm-mounting bracket of FIGS. 1 and 2;

FIG. 5A is a side view of a bolt in the structure of FIG. 5;

FIG. 6 is a view similar to FIG. 5 but for viewing from the side opposite that of FIG. 5; and FIG. 7 is a view similar to FIG. 2, to show a modification.

Figure 1:
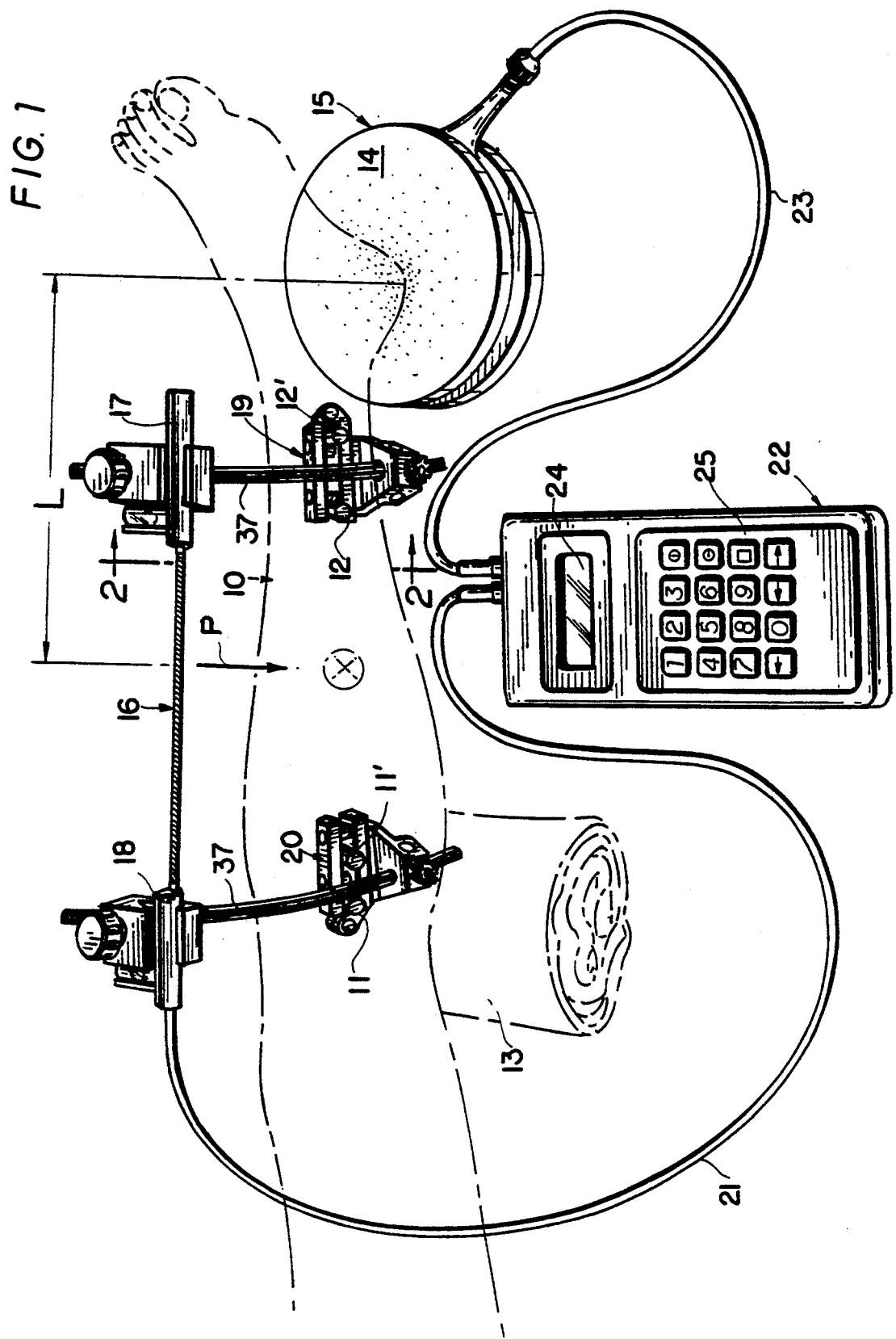
FIG. 1 is a simplified view in perspective, for the case of a bone-stiffness measuring device of the invention, in application to a patient having a fractured tibia at generally the location (X) in the drawing.

In the diagram of FIG. 1, the mark (X) generally designates the location of a tibia fracture in the left leg 10 of a patient who has experienced a normal and illustrative period of at least eight weeks following surgery wherein install two spaced bone screws 11, 11' were installed in the tibia and on the proximal side of the fracture location, plus two further bone screws 12, 12' installed in the tibia but on the distal side of the fracture location. These bone screws will be understood to have been part of the installation, setting and locking of an external fixator which has thus far been used to retain the fractured bone but which has now been temporarily removed from clamped engagement to the respective pairs of bone screws 11, 11' and 12, 12', for the purposes of a bone-strength measurement made with apparatus of the invention. The external fixator (not shown) may suitably be one of the Modulsystem fixators, manufactured by Orthofix S.r.l., of Verona, Italy, wherein each end of an elongate central body is connected by a ball joint to a bone-screw clamping device. These clamping devices are releasably fixed to the respective pairs of bone screws 11, 11' and 12, 12' in initially set and subsequently retained fixed orientation with respect to the central body, the orientation being retained by clamped settings of the respective ball joints. When the bone-screw clamps of the fixator are released, the settings of the ball-joint clamps of the fixator remain fixed, in readiness for accurate re-establishment of the external-fixator connection to the bone screws, once the brief measurement purposes of the invention have been served.

The patient may be lying flat in bed or seated on a bench, with his knee supported as by a tight roll 13 of towelling and his heel supported by the upper plate 14 of a load cell 15. The span between his points of heel and knee support is otherwise unsupported, the orientation of the foot being, in the form shown, upright and generally in a geometric vertical plane that includes the axis of the tibia and is or may be substantially normal to the horizontal plane defined by bone screws 11, 11', and substantially normal to the horizontal plane defined by bone screws 12, 12'. It is noted that these horizontal-plane relationships also generally accord with the course of the patient's adjacent fibula which, whether or not also fractured, is relatively flexible and therefore has inconsequential effect on vertical deflections involved in measuring tibia stiffness. It is further noted that vertically downward bending deflection of the tibia fracture at (X) may be in response to the physician's careful application of pressure P, as via the cupped palm of his hand and in the sagittal plane of the tibia.

Briefly, the apparatus to perform the stiffness measurement comprises an elongate goniometer 16 having distal and proximal end-mounting formations 17, 18, each of which is supported by one of two identical goniometer-support assemblies that are respectively anchored by bone-screw clamps 19, 20 to the externally projecting ends of bone screws 12, 12' and 11, 11'; detail of these identical support assemblies is provided below in connection with FIGS. 2 to 6. Goniometer 16 is shown to produce an electrical-signal output, via a flexible multi-conductor cable 21, to a battery-operated microcomputer unit 22 which is also supplied by an electrical-signal output in a second cable 23, from load cell 15. The microcomputer will be understood to be programmed for the calculation and display at 24 of instantaneously measured bending moment, preferably in Newton-meters per degree of bone-bending deflection, the calculation being performed pursuant to the two cable input signals, with dimensional factors, such as the horizontal distance L from the patient's heel to his fracture site (X) entered into the computer 22 via a push-button array panel 25, shown on the face of the computer.

More specifically, FIG. 2 illustrates supporting structure for the distal-end mount 17 of the goniometer unit 16. The bone screws 12, 12' remain, after fixator removal, to provide fixed anchoring reference to the distal stub of the fractured tibia bone 30. A bracket 31 is shown as a plate bent at about 45° to establish an end flat 32 that is drilled for clamping reference to the bone screws 12, 12'; at its other end, bracket 31 has an enlarged head 33, with two drilled orthogonally intersecting bores 34, 35 (see FIGS. 5 and 6). The bore 35 is on an axis contained within the vertical plane (36) of symmetry of bracket clamping to the bone screws 12, 12'; the plane 36 is also generally normal to the central axis of bone 30, and the axis of bore 34 is sloped at about 45° to the geometric plane of end flat 32. The bore 35 is normal to and through the vertical plane (36) of symmetry. A stiff arcuate rod 37, of curvature radius at least twice the diametral extent of bone 30, is of constant cross-section for piloting guidance in either of the bores 34, 35, and a knob-operated set screw 38, threaded to head 33 on a tapped-bore alignment (38') normal to both bores 34, 35, enables rod 37 to be clamped to bracket 31 regardless of which of these bores is selected for guidance of rod 37. Suitably, rod 37 is of hexagonal section, for effective binding and stabilizing engagement of set screw 38 thereto.

As seen in FIGS. 2, 5 and 6, the bone-screw clamp for bracket 31 comprises two elongate bars 40, 41 having engaged offsets at one end for their loose pivotal connection (at 42), the offset end of bar 40 being shown bifurcated for clevis-like reception of the offset end of bar 41 between the bifurcated formations of bar 40. The bars 40, 41 and the bracket end flat 32 have aligned bores for accommodation of two like clamp bolts 43. Detail for bolts 43 appears in FIG. 5A, it being noted that bolts 43 are threaded at their distal ends, exclusively for engagement to tapped bores only in bar 41; remaining length of the shanks of bolts 43 is unthreaded, for free axial passage through aligned smooth bores in bar 40, in end flat 32, and in optional spacer collars, as at 44 in FIG. 2. FIG. 2 will be seen as illustrating one relation of bone-screw clamp parts so as to mount bracket 31 below the level of bone-screw clamp action, while FIGS. 5 and 6 illustrate another relation of the clamp parts so as to mount bracket 31 above the level of bone-screw clamp action. Regardless of the selected arrangement, and when bolts 43 are secured, the loosely pinned relationship between bars 40, 41 enables the bars to equally share their clamp action against both of the bone screws 12, 12'.

FIGS. 3, 4 and 5 provide detail for flexibly adjustable means whereby each of the mounting ends 17, 18 of goniometer 16 can be readily and accurately positioned and oriented, for meaningful operation of the goniometer. The presently preferred goniometer, for which the triangular section shown at 17 is applicable, is one of the "Electrogoniometer" products of Penny & Giles Biometrics Ltd., of Blackwood, Gwent, Wales. Their electrogoniometers include single-axis, twin-axis and torsionally sensitive devices, of which the single-axis variety is satisfactory and preferred for purposes of the present description, in that the requisite bending for a stiffness measurement of bone 30 is desirably in a single vertical plane, namely, the sagittal plane of bone 30. It suffices to observe that the indicated single-axis goniometer comprises an elongate flat flexible strip of suitable plastic substrate material having strain-gage resistance wire or coating applied to its upper and lower surfaces, for inclusion in an electrical bridge circuit, which is resistance-sensitive to bending in the vertical plane. The end mount 18 which accommodates cable 21 is the end at which the proximal end of the goniometer strip is fixed. A closely wound coil of flexible, softly compliant wire is fixed at its proximal end to end mount 18 and at its distal end to end mount 17; this coil provides mechanical protection of the goniometer strip, which is freely guided by and within the flexible coil, the distal end of the goniometer strip being free of connection to and therefore slidably guided within the distal end mount 17.

For the indicated goniometer, the end-mount cross-sections are isosceles-triangular, with a flat base that must be vertical, in order to orient the goniometer strip for response to bending in the vertical plane. To assure such orientation, the body 46 of each of two duplicate mounting assemblies is generally rectangularly prismatic, as best seen in the isometric view of FIG. 3, wherein a three-axis directional legend X identifies the generally horizontal, longitudinal direction parallel to the axis of bone 30, Y identifies the strictly horizontal direction orthogonal to the X direction, and Z is the vertical direction, perpendicular to the horizontal plane established by directions X and Y. The prismatic body 46 is shown with a longitudinally extending edge which has been milled out in the X direction, at 47, to define guide-socket contouring for correct orientation of a longitudinally inserted one of the goniometer end mounts, with the triangular section of the end mount oriented to accommodate the rounded apex edge of the triangular section in an apex concave contour 48 of body 46, and with the base of the triangular section in retained location against the vertical flat surface 49 of the milled contour. A set screw 50 in a tapped bore through body 46 is driven to thrust an inserted triangular-section end mount of the goniometer into axially retained abutment with the apex concavity 48; such clamped retention applies for each of the respective end-mounting bodies 46, i.e., at the proximal and distal locations of goniometer mounting.

Each prismatic body 46 is shown to have been further milled out along an upper corner in the transverse or Y direction, to establish a local groove 51 which provides fixed seating support and location for a so-called spirit level 52, having an upwardly exposed air bubble indicator. Thus, as long as the air-bubble of the spirit level remains centered, it may be known that the goniometer strip is correctly oriented for electrical response to bending in the vertical plane.

To selectively position body 46 as needed, with respect to the stiff arcuate rod 37, an elongate mounting block 54 has a smooth elongate bore 55, and a set screw 56 (FIG. 2) in a tapped bore 57 (FIG. 3) is driven against rod 37 for retention of a laterally adjusted position. Block 54 mounts a ball 58 at the end of an upstanding stem 59, and ball 58 will be understood to be captive within a vertical bore 60 in body 46, wherein at least the upper end of the vertical bore is tapped for threaded reception of a knob-headed clamp screw 61 by which ball 58 and, therefore also body 46, may be fixed to hold a particular spirit-level (52) indication that the transverse horizontal orientation has been achieved.

FIG. 3 further illustrates that for more generalized use, the body 46 via which a transverse level is ascertainable is also milled out of the same X-direction upper corner as discussed in connection with contour 47, so as to establish an alternative goniometer-mounting profile 62 having a flat base orienting surface 63 that is perpendicular to the flat base orienting surface 49 of contour 47. A tapped bore 64 will be understood to extend vertically through body 46 such that a set screw (not shown) threaded to bore 64 may secure a triangular goniometer-end mount with location of its apex edge in the concave apex feature 65 of profile 62 with an internally directed rotation of the foot at about 15 degrees from the vertical, thus placing the fibula in substantially the same horizontal plane as the tibia. Thus alternatively mounted, a goniometer end mount 17' will have the appearance and orientation shown in FIG. 7, and the thus-mounted goniometer, if of single-axis variety, will be resistance-sensitive to bending deflection in the horizontal plane.

FIG. 7 further illustrates that the flat end 32' of a bracket 31' may itself be an element of the bone-screw clamping structure. As seen in FIG. 7, the flat end 32' of bracket 31' constitutes and takes the place of the bar 40 of FIGS. 5 and 6. The flat end 32' may optionally be pivotally connected to the bar 41 (having threaded bores), so that with bolts 43 through spaced smooth bores of flat end 32', the bracket 31' is immediately anchored directly to the clamped bone screws 11, 11' or 12, 12'.

USE OF THE INVENTION

1. The patient is made comfortable either in the seated position mentioned above, or lying flat on a firm bed. The patella and the foot should be facing upwards. The proximal end of the tibia is rested on a suitable support, as on the roll of towelling 13, or on a small sand bag from an operating theater. The load cell 15 is placed under the heel, such that the cell is secure, with the heel centered on the top plate 14. The tibia should be supported only at each end, leaving the intervening length unsupported and suspended, without touching the bed or anything else.

2. The number of weeks since fracture should be confirmed with the patient. The external fixator should not be removed short of eight weeks after injury, unless the surgeon has every confidence that the fracture will be stable. The fixator is removed by unlocking its bone-screw clamps, and caution is needed before fixator removal, to be sure of fixator orientation, in order to avoid later replacement upside down. Ball joints of the fixator should not be unlocked; their locked retention is a safeguard against a shift of bone position while making the stiffness measurement. As an added precaution, a small piece of tape adhered to one bone screw of each pair of bone screws provides a reference mark, applied prior to fixator removal and assuring accurate re-establishment of the fixator function.

3. It is worth taking a moment to check bone screw or pin sites carefully, now that the fixator has been removed. Each bone screw should be gently checked manually for possible looseness. The presence of loose screws does not affect accuracy of measurements, but precaution is necessary when applying bone-screw clamps for goniometer support.

4. If one or both bone screws (or either or both sides of the injury) is loose, the involved pair of bone screws should be pressed together under light pressure as the clamp is being set; this will establish a sufficiently rigid structure for the stiffness measurement. The brackets 31 with their rods 37 and blocks 54 should be preliminarily set so as to place the flat base reference surface 49 as nearly as possible in the vertical and in the sagittal plane of bone 30; this is done by loosely assembling each mounting end (17, 18) of the goniometer in the locating contour of the respective body contour 47. Each of these mounting ends has at least one part thereof projecting beyond body 46, so that the surgeon can adjust and fix the position of block 54 along rod 37 while orienting body 46 for a bubble indication of the level condition, and while also sighting along the flat base surface of the triangular section of mounts 17, 18 in succession, for centered sagittal-plane alignment with the tibia, as suggested by alignment 30' in FIG. 2. Having fixed the positions and orientation of goniometer end-mount support and orientation, the goniometer should be fixed at its proximal and distal end mounts, under slight tension of the protective wire coil, thus avoiding goniometer droop between its supported ends. This slight tension does not tense the goniometer, but it is a means of avoiding play in the event of slack in the wire coil. The spirit level 52 associated with each of the proximal and distal mounts of the goniometer, coupled with the sagittal-plane adjustment mentioned above, assures that the goniometer is in the correct plane when the spirit levels register horizontal. But it is noted that if the goniometer is not directly over the tibia, it is possible that some rotation may occur at the fracture-site, resulting in an erroneous stiffness measurement. Any rotation that occurs with the goniometer in the correct position will not be registered, because the rotation will be in the frontal plane; the goniometer will only register changes in the sagittal plane.

5. The cables 21 and 23 from the goniometer and from the load cell should now be connected to the microcomputer 22, and the latter should be switched on. As noted above, bone stiffness is measured as angular change, per unit load, with a length factor L reflecting distance from the measured load to the nearest point of weakness. The microcomputer 22 is programmed to compute and display bone stiffness, in Newton-meters, pursuant to the formula:

$$\text{STIFFNESS} = \frac{\text{FORCE times DISTANCE }(L)}{\text{ANGULAR DISPLACEMENT}}$$

Strictly speaking, the measured displacement should be linear, but since required angular measurement is small (<1°), measurement of angular displacement with a sensitive goniometer element of fixed length (as here) is inconsequentially different from a linear measurement of displacement.

6. It should be noted that when the area of bone weakness is not linear and transverse, the distance L entered at 22 should be the shortest distance from the heel to the area of bone weakness; this is to avoid a stiffness measurement that is artificially high. If the fracture is a segmental one, the measurement of L is to the most distal fracture. If there is a pair of bone screws in the central section of a segmental fracture, then it is possible to measure the stiffness of each fracture separately.

7. Having set the apparatus and the patient for a stiffness measurement, the presently preferred programmed succession of events is as follows:

(a) The first measurement is a test measurement, to confirm that the patient is comfortable.

(b) The start button at 25 is pressed to initiate the measurement.

(c) There is a short programmed delay to allow the surgeon to place his hand on the tibia over the fracture. The position of the hand is not critical, as long as it is between the two sets of screws 11, 11' and 12, 12'. The hand will be between the goniometer and the tibia.

(d) At a first programmed beep from the microcomputer, the surgeon starts to press on the leg. The object is to bend the bone between 0.5 and 1.0 degrees. If the stiffness is low, and the bone is in the early stages of healing, the pressure required will be slight. As the stiffness increases, the pressure will have to increase also, but it will be no more than the pressure that is required for a clinical assessment of healing. The numerical display at 24 will be an indication of the changing angle with a target change of 0.5°, and the microcomputer is programmed to sound an alarm if 1.0° is exceeded. The measurement is taken over a period of three seconds, and the aim should be to apply a steadily increasing pressure over this period of time, so that the angle can be observed to change throughout the test. Sudden movements should be avoided. The hand is removed after a second programmed beep is heard; this will be three seconds after the first beep.

(e) While performing the test measurement, the surgeon should watch the patient's face for signs of discomfort. A common fault for surgeons new to the technique is not to press hard enough. If the angle achieved is less than 0.5°, a repeat test measurement is requested, by programmed display at 24.

(f) If the test is satisfactory, the surgeon proceeds to perform five measurement procedures. If the patient and surgeon are confident with the procedure, then the surgeon can observe the change in angularion during the test to confirm that it is adequate.

(g) While the measurement is being performed, the microcomputer program correlates the change in angle with the change in load. This correlation is displayed as a coefficient with the stiffness measurement, and the surgeon has the opportunity to accept or reject each reading according to the correlation. In addition, the program will automatically reject any test with a coefficient of less than 0.900. With practice, it is possible for the surgeon to achieve correlations greater than 0.950, and this should be the aim.

(h) After five successive measurements, the microcomputer program provides a display at 24 of the average of the five readings. This average is the bone stiffness.

(i) If the result is less than 15 Nm/degree, the fixator is replaced carefully in the correct orientation. If the result is more than 15 Nm/degree, a decision should be made as to whether the fixator can be removed. As a final test, the screws can be left in for some hours or days without the fixator being attached, but the surgeon will not find that this is necessary as his confidence in the results increases.

Thus far, use of the described apparatus and technique have been primarily in application to the tibia, be it for stiffness measurement of a healing fracture or of an osteotomy. There has been some use on the femur but insufficient experience has accumulated to be able to set a level equivalent to the 15 Nm/degree value indicated above for the tibia. Use of the apparatus for femur measurements may be briefly summarized by the following procedural steps:

(a) The patient sits on a bed, and the femoral condyles are positioned over the load cell. The fixator is removed as for the tibia, and the goniometer is fixed above the femur in the sagittal plane. The measurement is performed in the same way as for the tibia.

(b) The goniometer is then moved to the lateral position in the frontal plane. The load cell is positioned medial to the condyles, and is held there by the surgeon or an assistant.

(c) The measurement is again performed, but this time with the load applied from the lateral side, to as to press the medial femoral condyle into the load cell.

(d) If X-ray viewing of the configuration of the callus suggests the need, the surgeon can then repeat the stiffness measurement from the medial side, with the load cell and goniometer positions reversed.

SUMMARY

The described stiffness measurement apparatus will be seen to meet all stated objects. The spirit-level location with respect for goniometer-mounting flats 49 and 63 assures the accurate positioning which is needed for high correlation between successive measurements. The surgeon can make an accurate graphical plot of his patient's periodically measured and developing bone repair, enabling enhanced confidence in his decision when to relieve the patient of external fixation, at a time prudently short of development of maximum stiffness int he repairing bone. For example, for the illustrative case of tibia repair, achievement of a measured stiffness of 15 Nm/degree is substantially short of the ultimate 50 to 60 +Nm/degree stiffness expected of a normal adult; for an overweight patient a slightly higher target stiffness level of 20 Nm/degree is recommended before relief from external fixation, but this is also short of the expected ultimate stiffness development.

The described apparatus lends itself not only to enhanced accuracy, and reliability of stiffness measurement, but also using a microcomputer 22 programmed as indicated, to complete, within six minutes, a full course of (a) test measurement, (b) five sequential stiffness-measurement cycles, (c) with computer-aided assurance of at least 0.900 correlation, and with an indicated display of the correlation between the five separate measurements, as well as their average, which can be visually observed and/or entered into temporary storage, for later offloading from the microcomputer to the surgeon's patient data bank.

Not the least of the reasons for an ability to complete all measurement tasks in six minutes, is the viewability of spirit level 52 adjacent an exposed portion of the flat vertical base of each goniometer-end mount, enabling a downward visual sighting which can be readily adjusted for sagittal-plane alignment with the patient's leg.

What is claimed is:

1. In combination, for use in duplicate in selective mounting of a bending-stress goniometer in an evaluation of the strength of a bone fracture which has been under external fixation for a period of bone-recovery time, wherein the external fixation has been between longitudinally spaced clamps each of which was fixed to externally projecting ends of at least two spaced bone screws, and wherein the external fixation and said spaced clamps have been removed for a goniometer evaluation of bone-strength; said combination comprising:

(a) a bone-screw clamp having two jaw members and two bolts on spaced alignments through both jaw members, for fixing said jaw members in simultaneous squeezing engagement with two bone screws on one longitudinal side of the fracture;

(b) a bracket having a flat base with bolt apertures spaced for registry with said bolts, whereby to clamp said base on one side of one of said jaw members upon securing said bone-screw clamp to the engaged two bone screws; said bracket having a headed body portion extending away from said base, said body portion having a bore inclined at an acute angle to the plane of said flat base;

(c) a stiff arcuate arm member of radius at least twice the diameter of the fractured bone, said arm member being adjustably positionable in the bore of said headed part, and selectively operable means for securing said arm member to said bracket in an adjusted position thereof; and (d) a goniometer-end mount having a selectively lockable ball-joint connection to a base unit, wherein the base unit has an elongate bore for adjustable positioning of said base unit along said arm member, and selectively operable means for clamping said base unit to said arm member in an adjusted position thereof.

2. The combination of claim 1, in which the headed body portion of said bracket is otherwise flat and extends at an acute angle from said base.

3. The combination of claim 1, in which said goniometer-end mount has a straight guide for generally horizontal reception and orientation of a goniometer end, with means carried by said mount for selectively fixed retention of the orientation of the goniometer end.

4. The combination of claim 3, in which an elongate bubble-sight level indicator is fixedly connected to said mount with its elongation axis substantially normal to the direction of said straight guide, whereby to establish a predetermined horizontal reference for subsequently stressed deflection of a mounted goniometer.

5. The combination of claim 1, in which said arm member is a rod of constant polygonal section.

6. The combination of claim 5, in which said constant polygonal section is hexagonal.

7. The combination of claim 5, in which said polygonal section is characterized by opposed parallel sides that respectively define concave and convex limiting surfaces of the arc of said rod.

8. The combination of claim 7, in which the selectively operable means for securing said rod to said bracket is a set-screw threaded to the headed part on an alignment parallel to the flat body part of said bracket and normal to the bore of said headed part.

9. The combination of claim 7, in which the selectively operable means for clamping said base unit to said rod is a set-screw threaded to said base unit on an alignment normal to said elongate bore.

10. The combination of claim 9, in which the base unit connected to said goniometer-end mount is via a ball-mounting stem anchored to said base unit on an axis normal to said elongate bore, the ball being captive in a seat formation of said goniometer-end mount.

11. The combination of claim 10, in which a set-screw is threaded to said goniometer-end mount on an alignment which intersects the ball center and is generally normal to a geometric plane established by the direction of said straight guide and by the elongation axis of said level indicator.

12. The combination of claim 3, in which said straight guide is adapted to support a goniometer-end fitting of constant isosceles-triangular section having a base that is larger than its two other sides, said straight guide having a section which conforms to one of said two sides and to at least a portion of the other of said two sides adjacent an apex connecting said two other sides, and selectively operable means including a set-screw threaded to said mount on an alignment normal to the base side of said triangular section for releasably clamping the goniometer-end fitting in fixed seated engagement with the other two side portions of said triangular section.

13. The combination of claim 12, in which said straight guide is one of two parallel straight-guide formations of said mount, wherein the selectively clamped orientation of the base of the triangular section in one of said straight-guide formations is normal to the selectively clamped orientation of the base of the triangular section in the other of said straight-guide formations.

14. The combination of claim 1, in which said jaw members are pivotally connected to each other at one longitudinal end thereof.

15. The combination of claim 1, in which the flat base of said bracket is one of said jaw members, whereby said bracket is an integral part of a portion of said bone-screw clamp.

16. A kit of adjustably connectable components for use in selective mounting of one of two longitudinal ends of a bending-stress goniometer in an evaluation of the strength of a bone fracture which has been under external fixation for a period of bone-recovery time, wherein the external fixation has been between longitudinally spaced clamps each of which was fixed to externally projecting ends of at least two spaced bone screws, and wherein the external fixation and said spaced clamps have been removed for goniometer evaluation of bone strength; said kit comprising:
  (a) a bone-screw clamp having two jaw men%bets and two bolts on spaced alignments through both jaw members, for fixing said jaw members in simultaneous squeezing engagement with two bone screws on one longitudinal side of the fracture;
  (b) a bracket having a flat base with bolt apertures spaced for registry with said bolts, whereby to clamp said base on one side of one of said jaw members upon securing said bone-screw clamp to the engaged two bone screws; said bracket having a headed body portion extending away from said base, said body portion having a bore inclined at an acute angle to the plane of said flat base;
  (c) a stiff arcuate arm member of radius at least twice the diameter of the fractured bone, said arm member being adjustably positionable in the bore of said headed part, and selectively operable means for securing said arm member to said bracket in an adjusted position thereof; and
  (d) a goniometer-end mount having a selectively lockable ball-joint connection to a base unit, wherein the base unit has an elongate bore for adjustable positioning of said base unit along said arm member, and selectively operable means for clamping said base unit to said arm member in an adjusted position thereof.

17. The kit of claim 16, in which the headed body portion of said bracket is otherwise flat and extends at an acute angle from said base.

18. The kit of claim 16, in which said goniometer-end mount has a straight guide for generally horizontal reception and orientation of a goniometer end, with means carried by said mount for selectively fixed retention of the orientation of the goniometer end.

19. The kit of claim 18, in which an elongate bubblesight level indicator is fixedly connected to said mount with its elongation axis substantially normal to the direction of said straight guide, whereby to establish a predetermined horizontal reference for subsequently stressed deflection of a mounted goniometer.

20. The kit of claim 16, in which said arm member is a rod of constant polygonal section.

21. The kit of claim 20, in which said constant polygonal section is hexagonal.

22. The kit of claim 20, in which said polygonal section is characterized by opposed parallel sides that respectively define concave and convex limiting surfaces of the arc of said rod.

23. The kit of claim 22, in which the selectively operable means for securing said rod to said bracket is a set-screw threaded to the headed part on an alignment parallel to the flat body part of said bracket and normal to the bore of said headed part.

24. The kit of claim 22, in which the selectively operable means for clamping said base unit to said rod is a set-screw threaded to said base unit on an alignment normal to said elongate bore.

25. The kit of claim 24, in which the base unit connected to said goniometer-end mount is via a ballmounting stem anchored to said base unit on an axis normal to said elongate bore, the ball being captive in a seat formation of said goniometer-end mount.

26. The kit of claim 25, in which a set-screw is threaded to said goniometer-end mount on an alignment which intersects the ball center and is generally normal to a geometric plane established by the direction of said straight guide and by the elongation axis of said level indicator.

27. The kit of claim 18, in which said straight guide is adapted to support a goniometer-end fitting of constant isosceles-triangular section having a base that is larger than its two other sides, said straight guide having a section which conforms to one of said two sides and to at least a portion of the other of said two sides adjacent an apex connecting said two other sides, and selectively operable means including a set-screw threaded to said mount on an alignment normal to the base side of said triangular section for releasably clamping the goniometer-end fitting in fixed seated engagement with the other two side portions of said triangular section.

28. The kit of claim 27, in which said straight guide is one of two parallel straight-guide formations of said mount, wherein the selectively clamped orientation of the base of the triangular section in one of said straight-guide formations is normal to the selectively clamped orientation of the base of the triangular section in the other of said straight-guide formations.

29. The kit of claim 16, in which said jaw members are pivotally connected to each other at one longitudinal end thereof.

30. The kit of claim 16, in which the flat base of said bracket is one of said jaw members, whereby said bracket is an integral part of a portion of said bone-screw clamp.

31. A kit according to claim 16, wherein the components (a), (b), (c) and (d) are in duplicate.

32. A kit according to claim 31, further comprising an elongate bending-stress goniometer having end fittings adapted for mounting in the straight guides of the respective duplicate mounts.

33. In combination, for use in duplicate in selective mounting of a bending-stress goniometer in an evaluation of the strength of a bone fracture which has been under external fixation for a period of bone-recovery time, wherein the external fixation has been between longitudinally spaced clamps each of which was fixed to externally projecting ends of at least two spaced bone screws, and wherein the external fixation and said spaced clamps have been removed for a goniometer evaluation of bone-strength; said combination comprising (a) a bone-screw clamp having two jaw members and two bolts on spaced alignments through both jaw members, for fixing said jaw members in simultaneous squeezing engagement with two bone screws on one longitudinal side of the fracture;

(b) a bracket having a flat base with bolt apertures spaced for registry with said bolts, whereby to clamp said base on one side of one of said jaw members upon securing said bone-screw clamp to the engaged two bone screws; said bracket having a headed body portion extending away from said base, said body portion having a bore inclined at an acute angle to the plane of said flat base;

(c) a stiff arcuate arm member of radius at least twice the diameter of the fractured bone, said arm member being adjustably positionable in the bore of said headed part, and selectively operable means for securing said arm member to said bracket in an adjusted position thereof; and (d) a goniometer-end mount having a ball-joint connection to a base unit, wherein the base unit has an elongate bore for adjustable positioning of said base unit along said arm member, and selectively operable means for clamping said ball-joint connection and for clamping said base unit to said arm member.

34. A kit of adjustably connectable components for use in selectively mounting of one of two longitudinal ends of a bending-stress goniometer in an evaluation of the strength of a bone fracture which has been under external fixation for a period of bone-recovery time, wherein the external fixation has been between longitudinally spaced clamps each of which was fixed to externally projecting ends of at least two spaced bone screws, and wherein the external fixation and said spaced clamps have been removed for goniometer evaluation of bone strength; said kit comprising:

(a) a bone-screw clamp having two jaw members and two bolts on spaced alignments through both jaw members, for fixing said jaw members in simultaneous squeezing engagement with two bone screws on one longitudinal side of the fracture;

(b) a bracket having a flat base with bolt apertures spaced for registry with said bolts, whereby to clamp said base on one side of one of said jaw members upon securing said bone-screw clamp to the engaged two bone screws; said bracket having a headed body portion extending away from said base, said body portion having a bore inclined at an acute angle to the plane of said flat base;

(c) a stiff arcuate arm member of radius at least twice the diameter of the fractured bone, said arm member being adjustably positionable in the bore of said headed part, and selectively operable means for securing said arm member to said bracket in an adjusted position thereof; and (d) a goniometer-end mount having a ball-joint connection to a base unit, wherein the base unit has an elongate bore for adjustable positioning of said base unit along said arm member, and selectively operable means for clamping said ball-joint connection and for clamping said base unit to said arm member.

35. In combination, for use in duplicate in selective mounting of a bending-stress goniometer in an evaluation of the strength of a bone fracture which has been under external fixation for a period of bone-recovery time, wherein the external fixation has been between longitudinally spaced locations each of which was fixed to externally projecting ends of at least two spaced bone screws, and wherein external fixation has been disconnected for a goniometer evaluation of bone-strength; said combination comprising:

(a) a goniometer-end mount adapted for longitudinally orienting one end of an elongate goniometer, said mount including level-sensitive indicating means for an alignment transverse to the mounted longitudinal orientation of a goniometer end;

(b) rigid base structure including selectively operable adjustable and releasably clampable means for rigid reference of said base unit to the bone screws at one of said locations; and (c) means including a selectively clampable ball-joint connection operative between said goniometer-end mount and said rigid base structure.

36. In combination, for use in duplicate in selective mounting of a bending-stress goniometer in an evaluation of the strength of a bone fracture which has been under external fixation for a period of bone-recovery time, (i) wherein the external fixation has been between longitudinally spaced clamps each of which has been fixed to externally projecting ends of at least two bone screws, (ii) wherein the respective clamps and their respective bone screws are at opposite longitudinal offset from the fracture, and (iii) where the external fixation has been disconnected for a goniometer evaluation of bone-strength; said combination comprising:

(a) a goniometer-end mount having upper structure for keyed longitudinal accommodation and for generally horizontal orientation of one end of an elongate goniometer in a vertical plane which includes the elongation axis of the bone;

(b) said mount having lower structure connected to said upper structure and including selectively adjustable and releasably clampable means for rigid bone-screw referenced positioning of said upper structure in external vertical offset above the bone and on the same longitudinal side of the fracture as the side of the associated bone screws; and (c) said mount further including level-sensing means adjacent said one end and oriented to sense tilt of said one end about the longitudinal axis at said one end.

37. In combination, for use in duplicate in selective mounting of a bending-stress goniometer in an evaluation of the strength of an elongate bone via first and second clamps which are referenced to the bone at longitudinally spaced locations along the bone, said combination comprising:

(a) a goniometer-end mount having upper structure for keyed longitudinal accommodation and for generally horizontal orientation of one end of an elongate goniometer in a vertical plane which includes the elongation axis of the bone between said spaced locations;

(b) said mount having lower structure connected to said upper structure and including selectively adjustable and releasably clampable means for rigid bone-screw referenced positioning said upper structure in external vertical offset above the bone at the longitudinal location of said one clamp; and (c) said mount further including level-sensing means adjacent said one end and oriented to sense tilt of said one end about the longitudinal axis at said one end.

38. In combination, for use in duplicate in selective mounting of a bending-stress goniometer in an evaluation of the strength of an elongate bone via first and second clamps which are referenced to the bone at longitudinally spaced locations along the bone, said combination comprising:

(a) a goniometer-end mount having first structure for keyed longitudinal accommodation and for generally horizontal orientation of one end of an elongate goniometer in a vertical plane which includes the elongation axis of the bone between said spaced locations;

(b) said mount having second structure connected to said first structure and including selectively adjustable and releasably clampable means for rigidly referenced connection to one of said clamps and positioning said first structure in external vertical offset with respect to the bone at the longitudinal location of said one clamp; and (c) said mount further including level-sensing means adjacent said one end and oriented to sense tilt of said one end about the longitudinal axis at said one end.

39. The combination of claim 38, in which the vertical offset of said first structure is above the bone.

40. A kit of adjustably connectable components for use in selective mounting of one of two longitudinal ends of a bending-stress goniometer in an evaluation of the strength of a bone fracture which has been under external fixation for a period of bone-recovery time, wherein the external fixation has been between longitudinally spaced locations each of which was fixed to externally projecting ends of at least two spaced bone screws, and wherein the external fixation has been disconnected for a goniometer evaluation of bone-strength; said kit comprising:

(a) a goniometer-end mount adapted for longitudinally orienting one end of an elongate goniometer, said mount including level-sensitive indicating means for an alignment transverse to the mounted longitudinal orientation of a goniometer end;

(b) rigid base structure including selectively operable adjustable and releasably clampable means for rigid reference of said base unit to the bone screws at one of said locations; and (c) means including a selectively clampable ball-joint connection operatively between said goniometer-end mount and said rigid base structure.

41. A kit of adjustably connectable components for use in selective mounting of a bending-stress goniometer in an evaluation of the strength of a bone fracture which has been under external fixation for a period of bone-recovery time, (i) wherein the external fixation has been between longitudinally spaced clamps each of which has been fixed to externally projecting ends of at least two bone screws, (ii) wherein the respective clamps and their respective bone screws are at opposite longitudinal offsets from the fracture, and (iii) wherein the external fixation has been disconnected for a goniometer evaluation of bone-strength; said kit comprising:

(a) a goniometer-end mount having upper structure for keyed longitudinal accommodation and for generally horizontal orientation of one end of an elongation goniometer in a vertical plane which includes the elongation axis of the bone;

(b) said mount having lower structure connected to said upper structure and including selectively adjustable and releasably clampable means for rigid bone-screw referenced positioning of said upper structure in external vertical offset above the bone and on the same longitudinal side of the fracture as the side of the associated bone screws; and (c) said mount further including level-sensing means adjacent said one end and oriented to sense tilt of said one end about the longitudinal axis at said one end.

42. A kit of adjustably connectable components for use in selective mounting of a bending-stress goniometer in an evaluation of the strength of an elongate bone via first and second clamps which are referenced to the bone at longitudinally spaced locations along the bone, said kit comprising:

(a) a goniometer-end mount having upper structure for keyed longitudinal accommodation and for generally horizontal orientation of one end of an elongate goniometer in a vertical plane which includes the elongation axis of the bone between said spaced locations;

(b) said mount having lower structure connected to said upper structure and including selectively adjustable and releasably clampable means for rigid bone-screw referenced positioning of said upper structure in external vertical offset above the bone at the longitudinal location of said one clamp; and (c) said mount further including level-sensing means adjacent said one end and oriented to sense tilt of said one end about the longitudinal axis at said one end.

43. A kit of adjustably connectable components for use in duplicate in selective mounting of a bending-stress goniometer in an evaluation of the strength of an elongate bone via first and second clamps which are referenced to the bone at longitudinally spaced locations along the bone, said kit comprising:

(a) a goniometer-end mount having first structure for keyed longitudinal accommodation and for generally horizontal orientation of one end of an elongate goniometer in a vertical plane which includes the elongation axis of the bone between said spaced locations;

(b) said mount having second structure connected to said first structure and including selectively adjustable and releasably clampable means for rigid bone-screw referenced positioning said first structure in external vertical offset with respect to the bone at the longitudinal location of said one clamp; and (c) said mount further including level-sensing means adjacent said one end and oriented to sense tilt of said one end about the longitudinal axis at said one end.

44. A kit according to claim 43, wherein the components (a), (b), and (c) are in duplicate.

45. A kit according to claim 44, further comprising an elongate bending-stress goniometer having end fittings adapted for mounting accommodation in the respective duplicate mounts.

* * * * *